United States Patent
Pya et al.

(10) Patent No.: US 11,723,773 B2
(45) Date of Patent: Aug. 15, 2023

(54) SURGERY FOR CORRECTING TRICUSPID VALVE REGURGITATION

(71) Applicant: "National Research Cardiac Surgery Center" NPJSC, Nur-Sultan (KZ)

(72) Inventors: Yuriy Pya, Nur-Sultan (KZ); Timur Lesbekov, Nur-Sultan (KZ); Aigerim Kunakbayeva, Nur-Sultan (KZ); Aigerim Kuzhakhmetova, Nur-Sultan (KZ)

(73) Assignee: "NATIONAL RESEARCH CARDIAC SURGERY CENTER" NPJSC, Nur-Sultan (KG)

( * ) Notice: Subject to any disclaimer, the term of this patent is extended or adjusted under 35 U.S.C. 154(b) by 224 days.

(21) Appl. No.: 17/347,982

(22) Filed: Jun. 15, 2021

(65) Prior Publication Data
US 2022/0395372 A1 Dec. 15, 2022

(51) Int. Cl.
*A61F 2/24* (2006.01)
(52) U.S. Cl.
CPC .......... *A61F 2/2463* (2013.01); *A61F 2/2466* (2013.01); *A61F 2220/0008* (2013.01); *A61F 2220/0075* (2013.01); *A61F 2230/0013* (2013.01)
(58) Field of Classification Search
CPC ............ A61F 2/2463; A61F 2220/0075; A61F 2230/0013; A61B 2017/0406; A61B 17/0401
See application file for complete search history.

(56) References Cited

U.S. PATENT DOCUMENTS

| | | | | |
|---|---|---|---|---|
| 7,959,674 B2* | 6/2011 | Shu | ........................ | A61F 2/2412 623/2.4 |
| 8,349,003 B2* | 1/2013 | Shu | ........................ | A61F 2/2412 623/2.4 |
| 10,568,740 B2* | 2/2020 | Lozonschi | ....... | A61B 17/00234 |
| 10,751,456 B2* | 8/2020 | Pya | ...................... | A61M 60/178 |
| 11,464,637 B2* | 10/2022 | Longoria | .......... | A61B 17/06166 |
| 11,529,233 B2* | 12/2022 | Keidar | .................. | A61F 2/2466 |
| 2019/0298904 A1* | 10/2019 | Pya | ...................... | A61M 60/148 |
| 2020/0146826 A1* | 5/2020 | Brunnett | ................ | A61F 2/2445 |

(Continued)

FOREIGN PATENT DOCUMENTS

CA 2902233 C * 1/2021 ......... A61B 17/0401

OTHER PUBLICATIONS

Besler, et al., Treatment options for severe functional tricuspid regurgitation: indications, techniques and current challenges, 16(31):1-16 (Nov. 2018).

(Continued)

*Primary Examiner* — Suzette J Gherbi
(74) *Attorney, Agent, or Firm* — Browdy and Neimark, PLLC

(57) ABSTRACT

A method is presented for tricuspid valve commissural annuloplasty for secondary tricuspid insufficiency. The method comprises suturing through a valve annulus, and bringing the valve annulus to its normal size while eliminating its regurgitation. The suturing comprises applying individual sutures on pledgets through the tricuspid valve annulus from a right ventricle side along anteroposterior and posteroseptal commissures on both sides of each of said commissures, spaced-apart from them; taking out needles of said sutures from a right atrium side and tying knots along the commissures between them.

5 Claims, 5 Drawing Sheets

(56) References Cited

U.S. PATENT DOCUMENTS

| | | | | |
|---|---|---|---|---|
| 2021/0093317 A1* | 4/2021 | Miraki | ............... | A61B 17/0467 |
| 2021/0161665 A1* | 6/2021 | Adams | ................. | A61F 2/2466 |
| 2021/0290391 A1* | 9/2021 | Subramanian | ..... | A61B 18/1492 |
| 2022/0257239 A1* | 8/2022 | Sauer, Md | ......... | A61B 17/0483 |
| 2022/0280318 A1* | 9/2022 | Sirhan | ....................... | A61F 2/89 |
| 2023/0069080 A1* | 3/2023 | Rao | .................... | A61B 17/0401 |

OTHER PUBLICATIONS

Boyd, et al., Tricuspid annuloplasty, Five and one-half years' experience with 78 patients, 68:3:344-351 (1974).

Ildar, et al., Abstract Attached, Surgical Treatment of Secondary Tricuspid Regurgitation by the Modified Suture Annuloplastic, Bulletin of modern clinical medicine, 11 (2):7-13 (2018).

Schofer, et al., First-in-Human Transcatheter Tricuspid Valve Repair in a Patient with Severely Regurgitant Tricuspid Valve, Journal of the American College of Cardiology, 65(12):1190-1195 (2015).

Taramasso, et al., Transcatheter tricuspid valve intervention: state of the art, EuroIntervention, pp. AA40-AA50, 2017.

Van Praet, et al., An overview of surgical treatment modalities and emerging transcatheter interventions in the management of tricuspid valve regurgitation, Expert Review of Cardiovascular Therapy, 16(20):1-36 (2018).

* cited by examiner

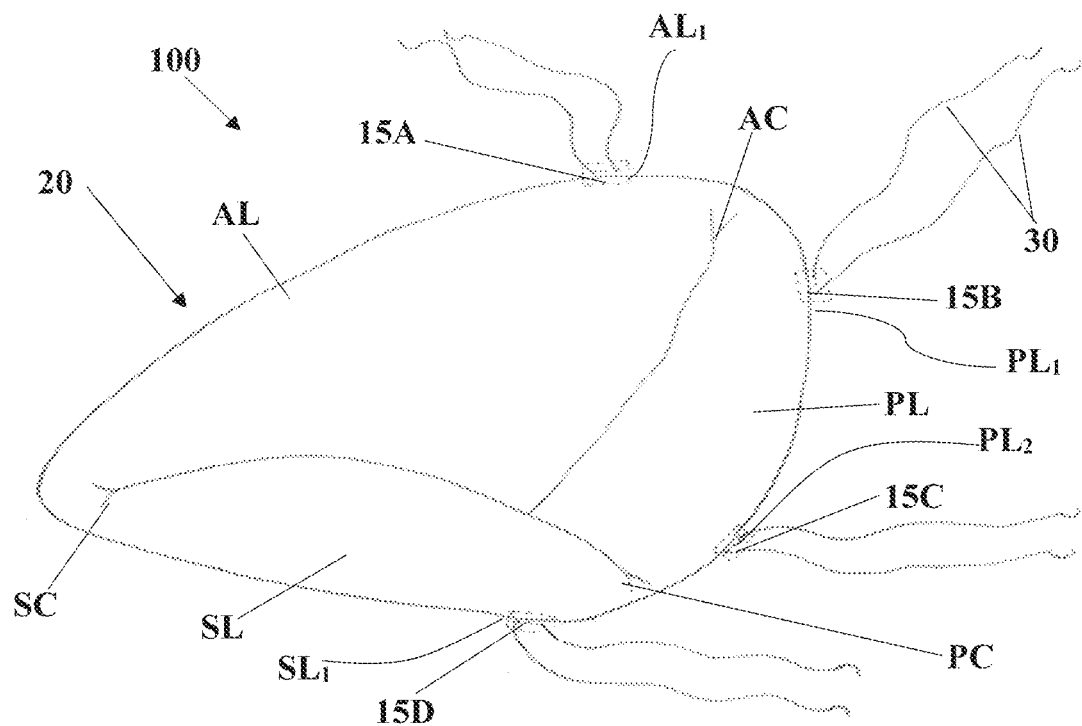
FIG. 2A
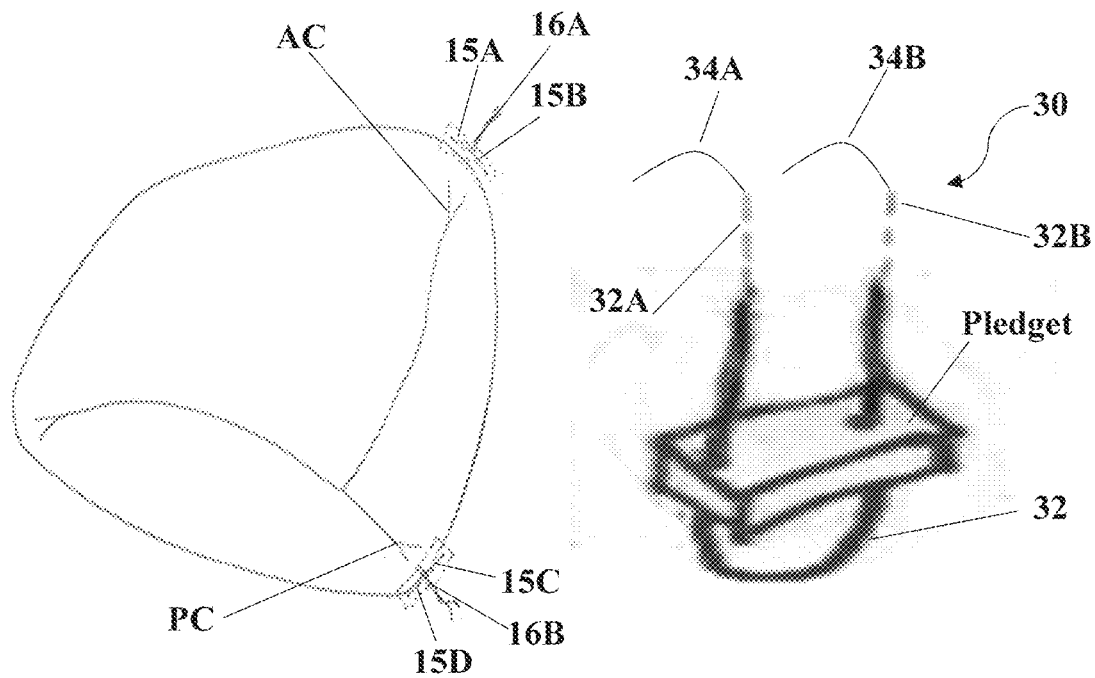
FIG. 2B
FIG. 2C
(GENERAL ART)

SURGERY FOR CORRECTING TRICUSPID VALVE REGURGITATION

TECHNOLOGICAL FIELD

The present invention is in the field of cardiac surgery methods/techniques. The invention relates in particular to a method for correction of tricuspid regurgitation of the tricuspid valve.

BACKGROUND

The tricuspid valve is the largest of the heart valves, located between the right ventricle and the right atrium and constituted by three leaflets named the anterior leaflet, septal leaflet, and posterior leaflet and three respective commissures named the anteroseptal, anteroposterior, and posteroseptal. The tricuspid valve serves as a one-way valve as to prevent backflow of blood into the right atrium during contraction of the right ventricle by closure of the valve (ventricular systole) between the right ventricle and the right atrium while allowing blood to flow from the right atrium into the right ventricle by opening of the valve (ventricular diastole).

Tricuspid regurgitation (TR), sometimes referred to as primary TR regurgitation, is a heart disease/disorder associated with incompletely closure of the tricuspid which results in formation of a space (i.e., orifice) between the leaflets. This affects the process where the three leaflets are to meet each other to close the valve during contraction of the right ventricle, and thus, some portion of blood, which must flow from right ventricle into the pulmonary artery flows backwards from the right ventricle to the right atrium through the orifice. Primary TR is caused by an abnormality of the tricuspid valve and/or its sub-valvular apparatus (tricuspid leaflets, chordae, papillary muscles, or annulus), due to congenital or acquired causes. Secondary (so-called 'functional') tricuspid regurgitation (TR) may originate, inter alia, from an annular dilatation of the tricuspid valve, which is usually secondary to left-sided valvular heart disease (especially affecting the mitral valve). More specifically, a normal tricuspid annulus has a non-planar, elliptical-shaped morphology, while the secondary TR causes the annulus to become dilated, namely, more planar and circular.

GENERAL DESCRIPTION

The present invention provides a novel surgical method for correcting tricuspid regurgitation disorders (e.g., secondary tricuspid regurgitation, which while being technically relatively simple, enables an improved tricuspid valve leaflet coaptation after the surgery while preserving tricuspid valve geometry, i.e., maintaining its tri-leaflet structure, a more stabilized annulus and preventing cardiac conduction system injury.

The most widely used conventional surgical techniques/methods of tricuspid regurgitation include annuloplasty ring implantation and suture annuloplasty techniques. These techniques are illustrated schematically in FIG. 1A and FIGS. 1B-1D, respectively.

FIG. 1A shows a ring annuloplasty technique in which a circular or semicircular ring RI is placed and stitched along the annulus of the tricuspid valve via appropriate stitches 10. Some of the disadvantages of this method are the technical complexity and the need for anticoagulant therapy in the postoperative period. Additionally, these techniques, are unpredictable and unreliable, owing to the long suture line and the ring material, which may break and slide through the tissue as the annulus dilates.

FIGS. 1B and 1C show the principles of one type of the known suture annuloplasty techniques, which are known as de Vega suture annuloplasty and modified de Vega suture annuloplasty, respectively. In the de Vega suture annuloplasty (FIG. 1B), a continuous doubled suture 10 is applied along the anterior and posterior portions of the annulus. Such suture 10 is commenced at the posterior extremity of the septal portion of the annulus and continues, in an anticlockwise direction, in the posterior and anterior portions of the annulus. At the commencement and the end of the suture, there is a pledget placed and affixed. In the modified version of the de Vega suture annuloplasty (FIG. 1C), which also utilizes a continuous suture, a plurality of Teflon pledgets 11 are interposed in each bite of the suture along a part of a circumference of the annulus via the continuous suture. The suture continues along the posterior and anterior annuli and ends in the central fibrous body, next to the anteroseptal commissure, resulting in a C-ring-type annuloplasty. Some of the drawbacks of these methods are the asymmetry of the applied suture, which entails deformation of the leaflets and the tricuspid valve annulus, resulting in unstable results.

FIG. 1D shows the principles of another type of the known suture annuloplasty techniques known as Kay annuloplasty. This technique includes placement of a pair of pledget-supported mattress sutures 10 in the vicinity of, respectively, the anteroposterior commissure and the posteroseptal commissure and coupling them together. As shown in the figure, this technique suffers from the tricuspid valve geometry change/violation, i.e., structural change of the valve due to deformation of the leaflets and/or tricuspid valve annulus resulting in change of its trileaflet form (e.g., change in geometry from oval to spherical shape), which may lead to unstable condition and cause postoperative complications that can eventually require reoperation.

As noted above, the novel approach of the present invention in surgical procedures of the kind specified provides for an improved tricuspid valve leaflet coaptation after the surgery while preserving tricuspid valve geometry. i.e., maintaining its tri-leaflet structure, a more stabilized annulus and preventing cardiac conduction system injury.

The present invention provides a method of the tricuspid valve commissural annuloplasty for secondary tricuspid insufficiency. According to this method, suturing through the valve annulus is performed, bringing the valve annulus to normal size with the elimination of its regurgitation. The sutures are applied through the tricuspid valve annulus from the right ventricle side along the anteroposterior and posteroseptal commissures on a pledgets (Teflon pledgets) on both sides of each commissure, slightly departing from them, taking out the needles from the right atrium side and tying knots along the commissures between themselves. A distance between each of the paired pledgets and the respective commissure may be about 0.8-1 cm.

The technique of the present invention is based on stitching of two pairs (generally at least two pairs) of a U-shaped pledged sutures on the bottom surface (located in the right ventricle) of the annulus of the tricuspid valve. The U-shaped pledged sutures of at least one first pair are located in a vicinity and at opposite sides of the anteroposterior commissure (AP commissure), respectively, one U-shaped pledged suture being at an anterior portion of the annulus associated with the anterior leaflet and the other U-shaped pledged suture being at a posterior portion of the annulus associated with the posterior leaflet. The U-shaped pledged sutures of the at least one second pair are located/stitched in a vicinity and at opposite sides of posteroseptal commissure (PS commissure), i.e. one of these second U-shaped pledged sutures being at a posterior portion of the annulus associated with the posterior leaflet and the other of the second U-shaped pledged suture of the pair being at a septal portion of the annulus associated with the septal leaflet.

The paired U-shaped pledged sutures are disposed on the annulus in the vicinity of and spaced-apart (at a certain distance) from the respective commissure at opposite sides thereof, and are then tied together resulting in folding of opposite tissue portions along the respective commissure towards the right ventricle facing one another. That is, each side of the respective commissure receives the U-shaped pledged sutures of the pair and the sutures of the pair are then stretched and pulled one towards the other and connecting between them by surgical knots.

It should thus be understood that, according to the present invention, the U-shaped pledged sutures are applied on both sides of the anteroposterior and posteroseptal commissures, since in the tricuspid regurgitation disorder the septal portion of the annulus is usually not involved in the dilation process and the tricuspid valve is often/typically dilated in these commissures, i.e. creation/origination of an orifice/space/gap due separation of respective leaflets.

It should be understood that the invention utilizes suturing technique in which at least two pairs of pledget-supported mattress suture (e.g. 3-0 Polipropelene sutures) are utilized, which when applied form U-shaped pledged sutures (cardiovascular sutures connected via a thread therebetween).

In some embodiments, in order to position the pledget-supported mattress sutures at their designated locations at the bottom surface (located in the right ventricle) of the annulus, the sutures can be delivered via the orifice of the regurgitated tricuspid valve.

Additionally or alternatively, a suitable delivery system, such as a transcatheter device (e.g., Trialign device) can be used to bring the pledget-supported sutures to the selected location. More specifically, the pledget-supported mattress sutures can be deployed by means of trans-jugular or trans-femoral venous approach. These catheter-based techniques are generally known and need not be described in details.

More specifically, according to the invention, the pledged sutures are applied from the right ventricle side of the heart, at locations slightly departing from the commissures, and passed through the tricuspid valve annulus so that the suture needles exit thereof from the right atrium side of the heart. To reduce the distance between each two adjacent leaflets, i.e., the distance between an anterior leaflet and a posterior leaflet and the distance between the posterior leaflet and a septal leaflet, surgical knots are performed at the anteroposterior commissure and the posteroseptal commissure, respectively, thereby increasing coaptation length between said adjacent leaflets. By tying the surgical knots, both sides of the respective commissure wherein pledged sutures were applied, are attracted one towards another and fastened permanently one to another. Such repositioning yields folding/plicating portions of each two adjacent leaflets that are formed towards the right ventricle side and increased coaptation length therebetween (e.g., during right ventricular contraction (i.e., systole) the gap between the leaflets is substantially reduced).

Thus, according to one broad aspect of the invention, there is provided a method for correcting secondary tricuspid regurgitation of a tricuspid valve, the method comprising:

providing at least four U-shaped pledget suture units forming at least first and second pairs of said units;

suturing first U-shaped pledget suture units of the first pair and second U-shaped pledget suture units of the second pair through the valve annulus at, respectively, predetermined first locations at opposite sides of an anteroposterior commissure and second locations at opposite sides of a posteroseptal commissure, such that said first units of the first pair are spaced-apart from the anteroposterior commissures at opposite sides thereof, and said second units of the second pair are spaced-apart from the posteroseptal commissures at opposite sides thereof; and tying the first units of the first pair between them by a first surgical knot across the anteroposterior commissure such that portions of anterior and posterior leaflets fold towards a right ventricle side of the tricuspid valve, and tying the second units of the second pair between them by a second surgical knot across the posteroseptal commissure such that portions of posterior and septal leaflets fold towards the right ventricle side of the tricuspid valve; thereby maintaining structural geometry of the tricuspid valve and eliminating its regurgitation.

Preferably, the suturing of each pair of the U-shaped pledget suture units comprises applying respective paired sutures to said locations through the tricuspid valve annulus from a right ventricle side along the anteroposterior and posteroseptal commissures on pledgets located to the right ventricle side of the annulus of the tricuspid valve on the opposite sides of the respective commissure, taking out needles of the U-shaped pledget suture units from a right atrium side and tying the surgical knots across the commissures between the units of the pair.

The pledgets are preferably made of Teflon material composition.

The tying of the first units of the first pair between them and tying of the second units of the second pair between them may be performed by stretching and pulling the units of the pair towards one another and forming the surgical knot.

According to another broad aspect of the invention, it provides a method of the tricuspid valve commissural annuloplasty for secondary tricuspid insufficiency, the method comprising suturing through a valve annulus, and bringing the valve annulus to its normal size while eliminating its regurgitation, wherein said suturing comprises applying individual sutures on pledgets through the tricuspid valve annulus from a right ventricle side along anteroposterior and posteroseptal commissures on both sides of each of said commissures, spaced-apart from them, taking out needles of said sutures from a right atrium side and tying knots along the commissures between them.

The cardiac surgery technique of the present invention provides for radical correction of secondary (functional) tricuspid regurgitation. This technique allows to provide: an adequate correction of secondary tricuspid insufficiency in patients with acquired heart valve diseases of the left heart side, complicated with pulmonary hypertension and tricuspid valve regurgitation due to annular dilatation: the stability of repair during the postoperative period; preservation of the tricuspid valve geometry, as close as possible to its normal anatomy; as well as safety of the cardiac conduction system during the surgery; and technical simplicity of the surgery.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A and 2B schematically illustrate the two main procedures according to the method of the present invention;

FIG. 2C exemplifies a typical U-shaped pledget suture unit suitable to be used in the technique of the present invention;

DETAILED DESCRIPTION OF EMBODIMENTS

Figure 1A:
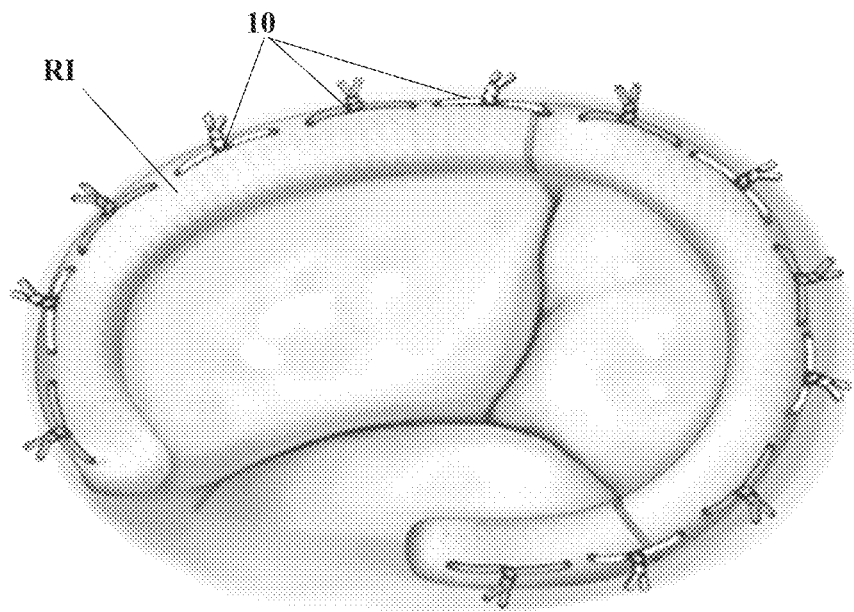
FIG. 1A schematically illustrates the principles of the known ring annuloplasty technique.
Figure 1B:
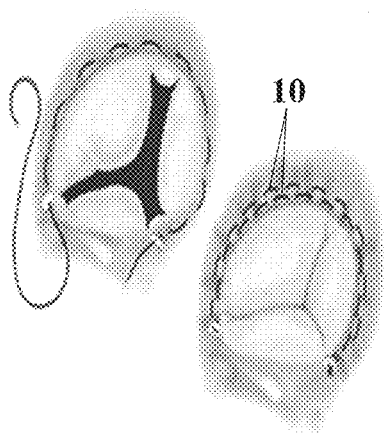
FIGS. 1B and 1C schematically illustrate the principles of de Vega suture annuloplasty and modified de Vega suture annuloplasty, respectively.
Figure 1C:
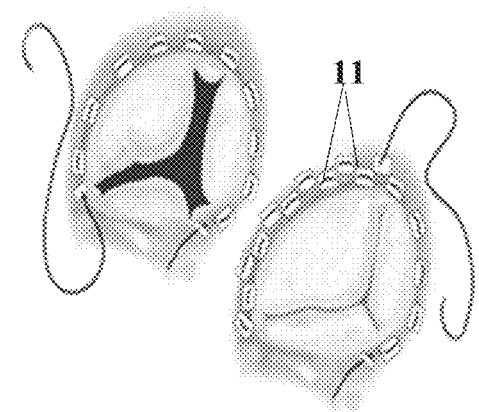
Figure 1D:
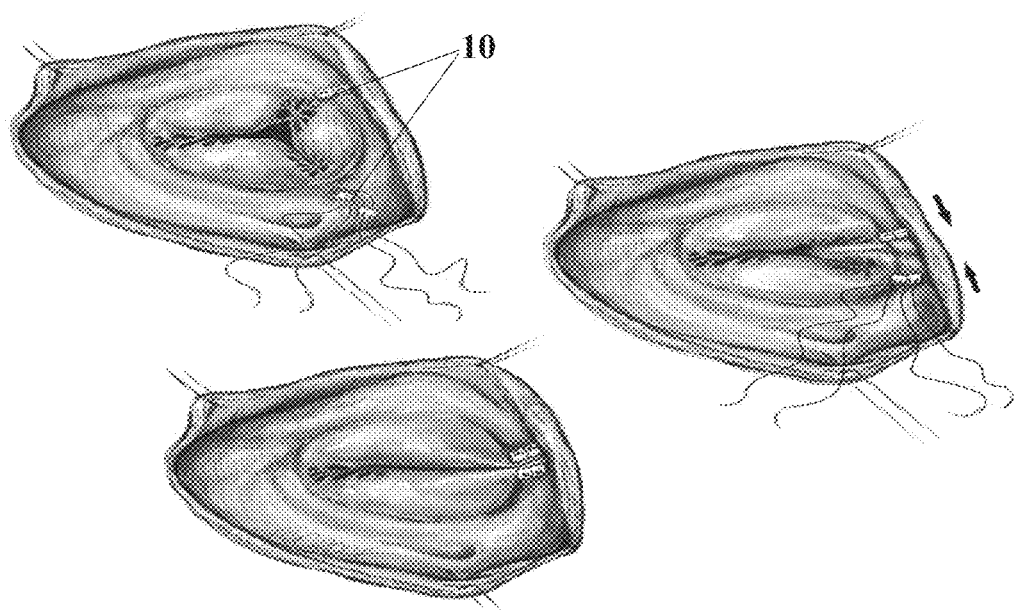
FIG. 1D schematically illustrates the principles of Kay annuloplasty technique.

FIGS. 1A-1D illustrate the known techniques for surgical methods for correcting tricuspid regurgitation disorders.

Reference is now made to FIGS. 2A and 2B schematically illustrating the two main procedures according to the method of the present invention. The figures show a top surface of a tricuspid valve 100 by which it faces the right atrium of the heart, namely, the right ventricle of the heart is located underneath said valve such that the bottom surface of the tricuspid valve 100 (not shown here) faces the right ventricle of the heart.

It should be noted that the terms "top surface" and "bottom surface" are used herein just in order to characterize/define the typical orientation of the tricuspid valve 100 with respect to the right atrium and right ventricle of the heart, and thus refer to the surfaces of the tricuspid valve 100 by which it faces the right atrium which is the upper chamber of the heart and the right ventricle which is the lower chamber of the heart, respectively.

The elements of the tricuspid valve 100 relevant for describing the technique of the invention include: an annulus 20 of the tricuspid valve; anteroposterior commissure AC; posteroseptal commissure PC; anteroseptal commissure SC; anterior leaflet AL; posterior leaflet PL; and septal leaflet SL.

As shown in FIG. 2A, the method of the present invention is performed by providing and stitching two pairs of U-shaped pledget sutures 15A-15B and 15C-15D (using the pledget-supported mattress sutures as described above). The pledgets are shown by dashed lines to emphasize that the U-shaped pledget sutures are applied to the respective regions of the tricuspid valve 100 from the bottom surface of the tricuspid valve (by which the valve faces the right ventricle of the heart).

The U-shaped pledget sutures 15A and 15B of a first pair are located at opposite sides of the anteroposterior commissure AC. The pledget of the suture 15A is stitched to the surface region $AL_1$ of the anterior leaflet AL of the annulus 20, and the pledget of the suture 15B is stitched to the surface region $PL_1$ of the posterior leaflet PL of the annulus 20, such that the paired pledgets are close to (in the vicinity of) and spaced-apart from the anteroposterior commissure AC.

The U-shaped pledget sutures 15C and 15D of the second pair are located at opposite sides of the posteroseptal commissure PC. The pledget of the suture 15C is stitched to a surface region $PL_2$ of the posterior leaflet PL, and the pledget of the other suture 15D of said pair is stitched to a surface region $SL_1$ of the septal leaflet SL, such that the paired pledgets are close to (in the vicinity of) and spaced-apart from the posteroseptal commissure PC (e.g. 0.8-1 cm distanced from the commissure).

As described above, the U-shaped pledged sutures (cardiovascular sutures connected via a thread therebetween) are of the type of pledget-supported mattress sutures. FIG. 2C exemplifies atypical U-shaped pledget suture unit 30 formed by a thread 32 which by its opposite ends 32A and 32B is connected to surgical needles 34A and 34B which, when piercing and passing through a pledget at two respective points on said pledget, define a U-shaped pledget suture unit.

After the U-shaped pledget sutures of each pair are deployed and stitched at their designated locations (as described above), the paired sutures are stretched and pulled one towards the other and connected/tied between them by surgical knots. In particular, to as shown in FIG. 2B, the paired U-shaped pledget sutures 15A and 15B, located in the vicinity of the anteroposterior commissure AC, are stretched and pulled towards each other and connected between them by surgical knot 16A, and the paired U-shaped pledget sutures 15C and 15D, located in the vicinity of posteroseptal commissure PC, are stretched and pulled towards each other and connected between them by surgical knot 16B.

As a result of the attachment of the paired sutures (by the surgical knots 16A and 16B), the distance between each two adjacent leaflets. i.e., the distance between the anterior leaflet AL and the posterior leaflet PL and the distance between the posterior leaflet PL and the septal leaflet SL, is reduced thereby increasing coaptation length between said adjacent leaflets.

Figure 3A:
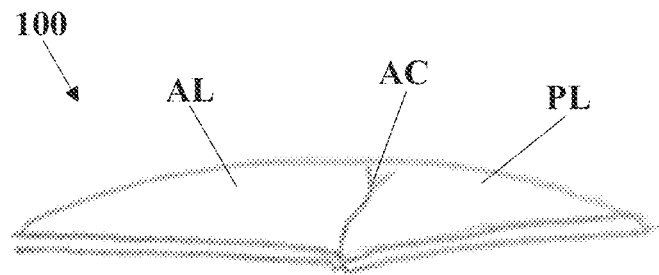
FIGS. 3A and 3B showing schematically a cross-sectional illustration of a portion/section of the tricuspid valve 100 prior to and after tying the pared sutures, respectively.
Figure 3B:
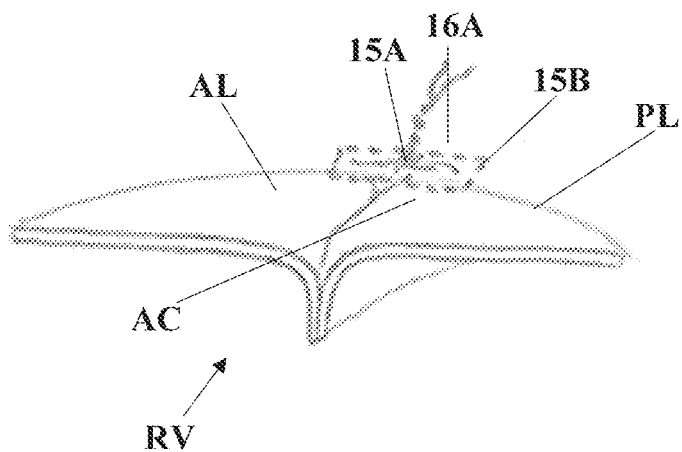

In this regard reference is made to FIGS. 3A and 3B showing schematically a cross-sectional illustration of a portion/section of the tricuspid valve 100 prior to and after tying the pared sutures, respectively. In these examples, the result of only one paired sutures coupling, associated with the anteroposterior commissure AC is shown. As seen in FIG. 3B, the surgical knot 16A of the U-shaped pledget sutures 15A and 15B yields folding/plicating portions of the two adjacent leaflets, i.e., the anterior leaflet AL and the posterior leaflet PL. Said portions are folded towards the right ventricle side RV of the heart thereby closing or at least significantly reducing an orifice (abnormal condition) and increasing coaptation length between these leaflets. By tying the surgical knot 16A, leaflets AL and PL at both sides of the anteroposterior commissure AC are attracted one towards the other and fastened permanently one to the other at generally single or possibly just a few discrete locations while leaving the free (not connected) facing portions thereof (i.e. the portions folded towards the right ventricle side RV. This results in the proper operation of the valve, while maintaining the geometry of the valve and substantially reducing the gap between the anterior leaflet AL and the posterior leaflet PL during right ventricular contraction (systole).

Annular distension also affects the commissures, mainly the anteroposterior and posteroseptal commissures (up to 30%) and to a lesser degree the anteroseptal commissure. Commissures that appear more like indentations than true commissures include the commissural leaflets and establish continuity between the three main leaflets of the tricuspid valve and ensure the competency of the tricuspid valve. By reduction of distentioned commissural part of the annulus, the physiologic continuity between leaflets is kept making them predisposed for coaptation. Moreover, this condition ensures the large surface of coaptation contributing to complete competency of the valve. Preserved cusps continuity and large coaptation surface achieved by commissural diving reduce the stress on the anatomical structures and therefore might predispose long term durability of the valve.

With respect to posterior leaflet it should be noted that its surface is smaller than anterior, but bigger than septal, and impacts on coaptation. The sutures are tied down, thus reducing the dilated annulus and ensuring adequate surface of coaptation, and the line of coaptation is trifurcated and slightly asymmetrical as in normal conditions.

Figure 4:
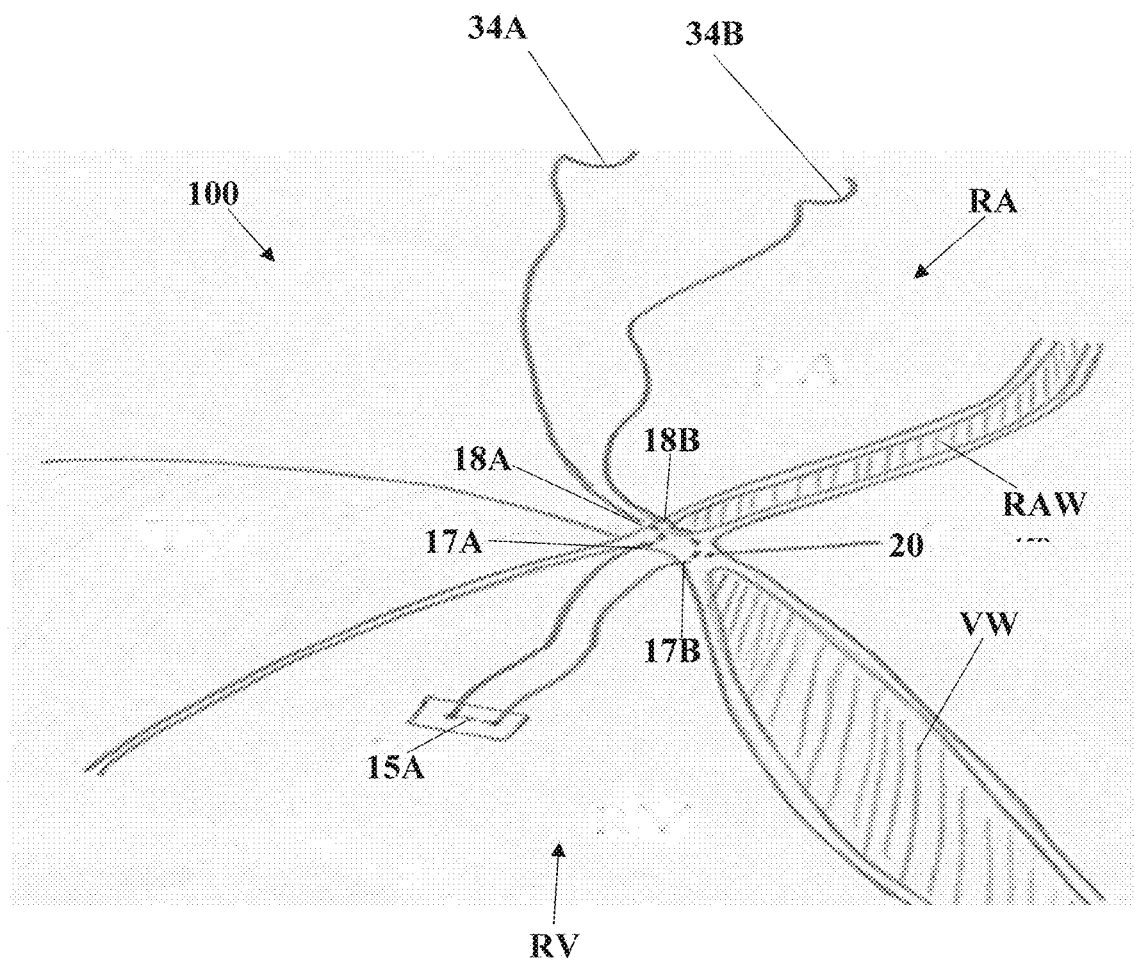
FIG. 4 shows more specifically the suturing technique of the present invention.

Reference is made to FIG. 4 showing more specifically the above-described suturing technique of the present invention, exemplified with respect to pledget-supported mattress suture (U-shaped pledget suture) 15A. As shows, the U-shaped pledget suture 15A is applied from the right ventricle side RV of the heart and passed through the tricuspid valve annulus 20 such that needles 34A and 34B exit/protrude to the right atrium RA side of the heart. As exemplified in the figure, the U-shaped pledget suture is placed between right atrium wall RAW and ventricular wall VW.

More specifically, the needles 34A and 34B of the U-shaped pledget suture 15A pierce the annulus 20 at two entering points 17A and 17B located on the bottom surface/side of the anulus 20, close to (in the vicinity of) and spaced-apart from the anteroposterior commissure, towards two respective exit points 18A and 18B on the upper surface/side of the annulus which faces the right atrium RA, thus forming the U-shaped suture that attaches the respective pledget to the bottom surface of the annulus after the sutures are pulled.

As mentioned above, in order to position the pledget-supported mattress sutures at their designated locations at the bottom surface (located in the right ventricle RV) of the annulus 20, the pledget-supported mattress suture can be delivered/deployed via the orifice of one of the dilatated commissures AC or PC of the regurgitated tricuspid valve.

It should be noted, although not specifically illustrated that the pledget-supported mattress sutures can be brought to the selected locations, where they are to be stitched/sewed, using a trans-jugular venous approach, i.e. using a suitable catheter-based delivery system, such as a transcatheter device (e.g., Trialign device).

The technique of the present invention has undergone clinical study on a number of patients, and some of the clinical study results are presented herein below.

Patient number 1, G., 52 y.o., diagnosis: Mitral valve insufficiency, D grade (AHA/ACC), I-II type by Carpentier. Tricuspid valve insufficiency, C grade (AHA/ACC). According to transthoracic echocardiography before surgical correction, LVEF was 68%, LV EDV 170 ml, ESD 4.7 cm, EDD 6.3 cm. Mitral valve annulus was 4.5 cm, tricuspid valve—4.1 cm. EMK 2.0 m/s, AMK 0.59 m/s, ETK 0.6 m/s, ATK 0.4 m/s, RV (BP) 3.0 cm. There was mitral valve posterior leaflet prolapse in the P2 zone, marginal chords detachment, severe mitral regurgitation, and VC 0.8 cm. Tricuspid regurgitation was severe.

The patient underwent surgery for repairing themitral valve (neochord formation in the P2-P3 zone, mitral valve annuloplasty with a "Sorin Carbomedics Annuloflex ring" number 30) and suturetricuspid valve commissural annuloplasty. Immediately after the end of the main stage of the operation and restoration of cardiac activity, a nodal rhythm was obtained with a heart rate of 40 beats per min. During an anti-inflammatory therapy in the early postoperative period the sinus rhythm was restored, which was preserved both in the early and long-term postoperative period. The patient was discharged on the 6th day after surgery having sinus rhythm.

In 3 months after surgery, according to transthoracic echocardiography, mitral valve repair was stable, the tricuspid valve leaflets coaptation length was 0.9 cm, the coaptation depth was 0.5 cm, and the tenting area was 0.7 cm2. TAPSE—1.6 cm. Tricuspid valve repair was stable. TR 0. 1 year after surgery, the tricuspid valve leaflets coaptation length was 0.9 cm. The tricuspid valve repair was stable. TR 0.

Patient number 2, F., 28 y.o., diagnosis: Constrictive pericarditis. Mitral valve insufficiency, D grade (AHA/ACC), I type by Carpentier. Tricuspid valve insufficiency, C grade (AHA/ACC).Paroxysmal atrial fibrillation. EHRA IIa. According to transesophageal echocardiography before surgical correction, MR was severe, VC 0.77 cm, MV annulus diameter 4.2 cm, LVEF 53%, LV EDV 53 ml, ESD 4.7 cm, EDD 5.2 cm. Tricuspid valve annulus was 4.1 cm, ETK 0.62 m/s, RV (BP) 3.0 cm. Tricuspid regurgitation was severe.

The patient underwent surgery. Subtotal pericardiectomy, mitral valve repair with «Sorin Carbomedics Annuloflex ring» number 32 implantation, suture commissural annuloplasty of the tricuspid valve. The patient was discharged on the 11th day after surgery having sinus rhythm. According to transthoracic echocardiography, at the time of discharge, mitral and tricuspid valve repair were stable.

1 year after surgery: LVEF 66%, LV EDV 108 ml, LV ESV 3.4 cm, LV EDD 5.0 cm, SV 71 ml, EMK 1.5 m/s, ETK 1.2 m/s. PG max 6 mmHg, PG mean 3 mmHg. Mitral and tricuspid valve repair were stable.TR 0. Sinus rhythm, CO 3.4 l/min, CI 2.0 l/min/m2.

Clinical case number 3: Patient M., 53 y.o., diagnosis: CHD. Atrioventricular septal defect, intermediate form. Mitral valve insufficiency. D grade (AHA/ACC). Tricuspid valve insufficiency, C grade (AHA/ACC).

According to transesophageal echocardiography before performing surgical correction, the primary ASD was 0.8-0.9 cm with a left to right shunt. The VSD was spontaneously closed by the soldered septal leaflet of the tricuspid valve. A cleft of the anterior leaflet mitral valve with severe mitral regurgitation was presented. LV EF 64%, LV EDV 67 ml, ESD 3.4 cm, EDD 4.9 cm, sPAP 60 mm Hg, RV (BP) 3.1 cm. Tricuspid regurgitation was severe.

The patient underwent surgery for repairing the mitral valve (anterior leaflet cleft suturing, suture annuloplasty in the A1-P1 zone), tricuspid valve suture commissural annuloplasty, primary ASD closure with an autopericardial patch. The patient was discharged on the 5th day after the operation in a satisfactory condition. 6 months after the operation, according to the transthoracic echocardiography data, mitral and tricuspid valve repair were stable. LVEF 67%, LV EDV 63 ml, LV ESD 1.7 cm, LV EDD 2.6 cm, SV 42 ml, EMK 1.0 m/s, AMK 0.43 m/s, ETK 0.77 m/s, ATK 0.34 m/s. sPAP 18 mm Hg, MV annulus diameter 2.7 cm, TV annulus diameter 1.9 cm. TAPSE 1.6 cm. TR 0. Tricuspid valve leaflets coaptation length was 1.1 cm, coaptation depth was 0.7 cm, the tenting area was 1.1 cm2.

This method of tricuspid valve commissural annuloplasty was performed in 22 patients (12 men and 10 women) at the NRCSC, who underwent open cardiac surgery, the average age of patients was 54.1 years (28-77 years). Degenerative valve pathology was in 40.9% (9), rheumatic lesion of left side valves was in 40.9% (9), congenital heart diseases was in 13.7% (3), constrictive pericarditis related tricuspid regurgitation was in 4.5% (1). In addition to the tricuspid valve suture commissural annuloplasty, the following procedures were performed: MV repair—45.5% (10), MV replacement—31.8% (7), MV and AV replacement—18.2% (4), ASD closure—9, 1% (2), CABG—13.6% (3), subtotal pericardiectomy—4.5% (1). According to transthoracic echocardiography, the average size of the tricuspid valve before surgery was 4.2 cm, TR ++ (moderate to severe TR).

All 22 patients were followed up for an average of 6 months after surgical treatment. According to the transthoracic echocardiography data 3 and 6 months after surgery, the average size of the tricuspid valve annulus was 3.15 cm and 3.0 cm, tricuspid regurgitation degree was minimal in both, average tricuspid valve leaflets coaptation was 0.76 cm and 0.7 cm respectively. This observation shows that the short-term results of the tricuspid valve suture commissural annuloplasty are satisfactory.

Thus, the novel approach of the present invention in surgical procedures of the kind specified provides for an adequate correction of secondary tricuspid insufficiency in patients with acquired left side valve diseases, complicated with pulmonary hypertension and tricuspid valve regurgitation due to annular dilatation while preserving tricuspid valve geometry. i.e., maintaining its tri-leaflet structure, a more stabilized annulus during the postoperative period and preventing cardiac conduction system injury.

The invention claimed is:

1. A method for correcting secondary tricuspid regurgitation of a tricuspid valve, the method comprising:
   providing at least four U-shaped pledget suture units forming at least first and second pairs of said units;
   suturing first U-shaped pledget suture units of the first pair and second U-shaped pledget suture units of the second pair through the valve annulus at, respectively, predetermined first locations at opposite sides of an anteroposterior commissure and second locations at opposite sides of a posteroseptal commissure, such that said first units of the first pair are spaced-apart from the anteroposterior commissures at opposite sides thereof, and said second units of the second pair are spaced-apart from the posteroseptal commissures at opposite sides thereof; and
   tying the first units of the first pair between them by a first surgical knot across the anteroposterior commissure such that portions of anterior and posterior leaflets fold towards a right ventricle side of the tricuspid valve, and tying the second units of the second pair between them by a second surgical knot across the posteroseptal commissure such that portions of posterior and septal leaflets fold towards the right ventricle side of the tricuspid valve; thereby maintaining structural geometry of the tricuspid valve and eliminating its regurgitation.

2. The method according to claim 1, wherein said suturing of each pair of the U-shaped pledget suture units comprises applying respective paired sutures to said locations through the tricuspid valve annulus from a right ventricle side along the anteroposterior and posteroseptal commissures on pledgets located to the right ventricle side of the annulus of the tricuspid valve on the opposite sides of the respective commissure, taking out needles of the U-shaped pledget suture units from a right atrium side and tying the surgical knots across the commissures between the units of the pair.

3. The method according to claim 1, wherein the pledgets are made of Teflon material composition.

4. The method according to claim 1, wherein the tying of the first units of the first pair between them and tying of the second units of the second pair between them comprises stretching and pulling the units of the pair towards one another and forming the surgical knot.

5. A method of tricuspid valve commissural annuloplasty for secondary tricuspid insufficiency, the method comprising suturing through a valve annulus, and bringing the valve annulus to its normal size while eliminating its regurgitation, wherein said suturing comprises applying individual sutures on pledgets through the tricuspid valve annulus from a right ventricle side along anteroposterior and posteroseptal commissures on both sides of each of said commissures, spaced-apart from them, taking out needles of said sutures from a right atrium side and tying knots along the commissures between them.

* * * * *